US010401341B2

United States Patent
Rella

(10) Patent No.: US 10,401,341 B2
(45) Date of Patent: Sep. 3, 2019

(54) SCANNED 1-D GAS ANALYSIS CAMERA HAVING A LINE PIXEL WEIGHTED FOR WIND SPEED

(71) Applicant: Picarro, Inc., Santa Clara, CA (US)

(72) Inventor: Chris W. Rella, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 663 days.

(21) Appl. No.: 14/534,022

(22) Filed: Nov. 5, 2014

(65) Prior Publication Data

US 2015/0059444 A1    Mar. 5, 2015

Related U.S. Application Data

(63) Continuation-in-part of application No. 13/934,023, filed on Jul. 2, 2013.

(60) Provisional application No. 61/740,896, filed on Dec. 21, 2012, provisional application No. 61/820,926, filed on May 8, 2013.

(51) Int. Cl.
| | |
|---|---|
| *G01N 33/00* | (2006.01) |
| *G01N 1/02* | (2006.01) |
| *G01N 1/22* | (2006.01) |
| *G01N 1/26* | (2006.01) |

(52) U.S. Cl.
CPC .......... *G01N 33/0011* (2013.01); *G01N 1/02* (2013.01); *G01N 1/2273* (2013.01); *G01N 1/26* (2013.01)

(58) Field of Classification Search
CPC .......... G01N 1/2273; G01N 1/02; G01N 1/26
See application file for complete search history.

(56) References Cited

U.S. PATENT DOCUMENTS

| | | | | |
|---|---|---|---|---|
| 4,135,092 A | * | 1/1979 | Milly ................. | G01N 33/0031 250/338.5 |
| 5,702,506 A | * | 12/1997 | Shih ...................... | B01D 46/12 55/343 |

(Continued)

OTHER PUBLICATIONS

Lamb et al., Development of Atmospheric Tracer Methods to Measure Methane Emissions from Natural Gas Facilities and Urban Areas, Environ. Sci. Technol., vol. 29, No. 6, pp. 1468-1479, (published 1995).*

(Continued)

*Primary Examiner* — Leslie J Evanisko
*Assistant Examiner* — Quang X Nguyen
(74) *Attorney, Agent, or Firm* — Lumen Patent Firm

(57) ABSTRACT

A gas concentration image (i.e., concentration vs. position data) in a cross section through a gas plume is obtained. Such measurements can be obtained by using a 2D array of gas sample inlets, or by moving a 1D array of gas sample inlets through the gas plume. By combining a gas concentration image with ambient flow information through the surface of the gas concentration image, the leak rate (i.e., gas flux) from the leak source can be estimated. Gas samples are simultaneously acquired by filling two or more gas sample storage chambers. This is the default operation mode, which is convenient to regard as recording mode. The other operating mode is a playback mode, where the gas samples in the gas sample storage chamber are sequentially provided to a gas analysis instrument. Gas collection via line pixels can be used to compensate for vertical wind speed variation.

16 Claims, 9 Drawing Sheets

(56) References Cited

U.S. PATENT DOCUMENTS

2012/0079871 A1* 4/2012 Williamson ....... G01N 15/0656
73/28.01
2016/0091476 A1 3/2016 Fischer

OTHER PUBLICATIONS

Lamb et al., "Development of atmospheric tracer methods to measure methane emissions from natural gas facilities and urban areas", 1995, Environ. Sci. Technol. v29, pp. 1468-1479.
McManus et al., "Atmospheric methane measurement instrument using a Zeeman-split He—Ne laser", 1989, Applied Optics v28n23, pp. 5016-5023.

* cited by examiner

SCANNED 1-D GAS ANALYSIS CAMERA HAVING A LINE PIXEL WEIGHTED FOR WIND SPEED

CROSS REFERENCE TO RELATED APPLICATIONS

This application is a continuation in part of U.S. Ser. No. 13/934,023 filed Jul. 2, 2013, and hereby incorporated by reference in its entirety. Application Ser. No. 13/934,023 claims the benefit of U.S. provisional patent application 61/740,896, filed on Dec. 21, 2012, and hereby incorporated by reference in its entirety. Application Ser. No. 13/934,023 also claims the benefit of U.S. provisional patent application 61/820,926, filed on May 8, 2013, and hereby incorporated by reference in its entirety.

FIELD OF THE INVENTION

This invention relates to gas handling for measurement of gas plumes in an ambient.

BACKGROUND

Methods for detecting gas leaks in ambient air have been investigated for many years. One of the basic problems of such measurements is to determine an estimate of the total gas leak rate from the leak source. A single point gas concentration measurement is not sufficient to determine the total gas leak rate. For example, a single measurement of a high gas concentration could mean the measurement point is very close to a relatively small leak, or some distance away from a large gas leak.

Accordingly, multi-point measurement techniques for gas leak detection have been investigated. U.S. Pat. No. 8,190,376 is a representative example. In this work, two or more gas concentration sensors are disposed in a region of interest, and these concentration measurements are combined with meteorological information (wind speed, direction and stability) to provide estimates of leak rate and leak location. A similar approach is considered in U.S. Pat. No. 6,772,071.

Although this approach can work well for leak detection in a fixed location, e.g., in a chemical plant, it is often necessary to perform leak detection from a mobile platform such as a moving vehicle. One important application of mobile gas leak detection is detecting leaks in natural gas utility distribution systems. For mobile gas leak detection, it is not usually possible to have several gas concentration sensors disposed around the location of possible gas leaks, thereby making the above-described approach inapplicable.

Accordingly, it would be an advance in the art to provide improved gas leak measurements, especially from a mobile platform.

SUMMARY

The present approach is based on the idea of obtaining a gas concentration image (i.e., concentration vs. position data) in a cross section through a gas plume. Such measurements can be obtained by using a 2D array of gas sample inlets, or by moving a 1D array of gas sample inlets through the gas plume. For example, the 1D array of gas sample inlets could be disposed on a mast affixed to a vehicle. By combining a gas concentration image with ambient flow information through the surface of the gas concentration image, the leak rate (i.e., gas flux) from the leak source can be estimated.

Gas samples are simultaneously acquired by filling gas sample storage chambers (one gas sample storage chamber for each of the gas sample inlets). This is the default operation mode, which is convenient to regard as recording mode. The other operating mode is a playback mode, where the gas samples in the gas sample storage chamber are sequentially provided to a gas analysis instrument. Triggering from the recording mode to the playback mode can be based on ancillary measurements (e.g., detection of an above baseline gas concentration).

In this manner, the expense of having one gas analysis instrument for each of the measurement points can be avoided. Another advantage of the present approach is that using a single analysis instrument means that cross-calibrating multiple analysis instruments is not required. An important feature of this approach is that it does not require sensors to be disposed around the location of a possible gas leak. Instead, measurements all from one side of the gas leak can suffice, provided the measurement points include a good cross section of the gas plume.

In some preferred embodiments, gas collection via line pixels can be used to compensate for vertical wind speed variation.

DETAILED DESCRIPTION

Figure 1A:
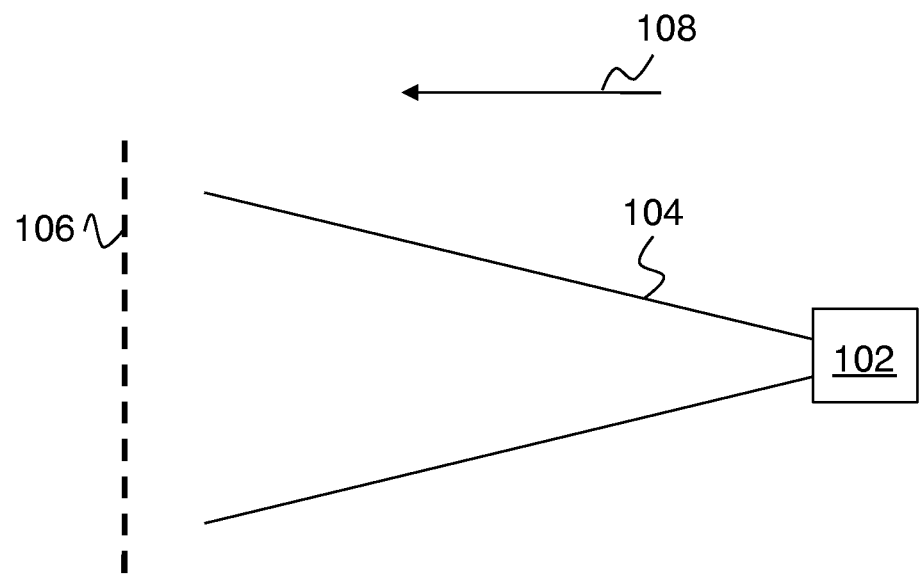
FIG. 1A shows a side view of a gas plume.
Figure 1B:
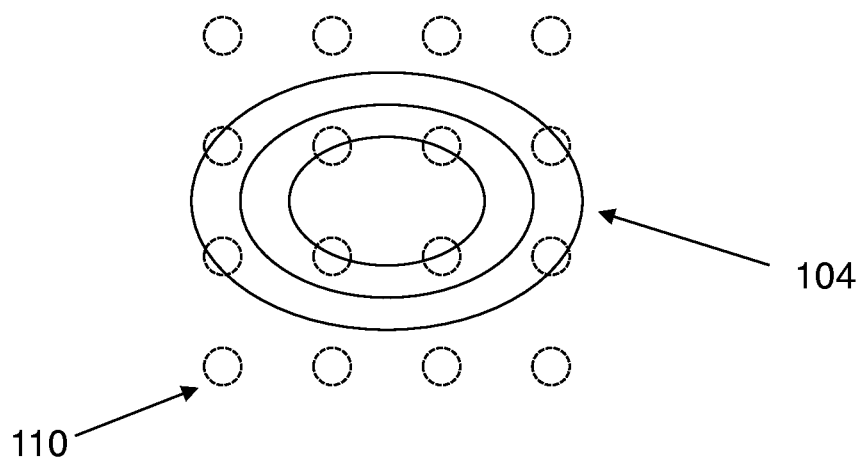
FIG. 1B shows an end view of the gas plume of FIG. 1A.

FIG. 1A shows a side view of a gas plume. FIG. 1B shows an end view of the gas plume of FIG. 1A. Here 102 is a source of a gas leak, which leads to a gas plume 104 as driven by an ambient wind 108. A smooth vertical surface 106 intersects the gas plume 104. FIG. 1B shows a view in the plane of surface 106, where measurement points 110 (dotted lines) overlap with the plume 106.

Consider a planar (or other) surface, through which one wants to measure the flux of molecules. The flux of molecules through the plane is given by the following integral:

$$Q(t) = \int_A k(C(x, y, t) - C_0)\vec{u}(x, y, t) \cdot \hat{n}\, dA \tag{1}$$

where $C(x,y,t)$ is the concentration at a given point in space on the surface A at time t, $C_0$ is the background concentration of the target gas in the ambient, $\vec{u}(x,y,t)$ is the velocity of the gas through the surface, and $\hat{n}$ is the normal to the surface element dA. The constant k converts volumetric flow in $m^3/s$ to moles/s, such that the units of emission Q(t) are, for example, moles/second. In this manner, gas concentration image measurements can be related to the total emission Q(t) from the leak source.

As indicated above, and described in greater detail below, gas samples are acquired simultaneously into two or more gas sample storage chambers, and then provided sequentially to a gas analysis instrument. Thus an exemplary method includes the following steps:

1) simultaneously collecting two or more gas samples in two or more gas sample storage chambers, where the gas sample storage chambers receive input gas from two or more measurement locations, and where the measurement locations are configured to be on a smooth vertical surface;
2) providing the two or more gas samples sequentially to a gas analysis instrument to provide gas concentration data points;
3) relating the gas concentration data points to the two or more measurement locations to provide a gas concentration image of the smooth vertical surface; and
4) providing the gas concentration image as an output.

Optionally, the further steps of: 5) obtaining an estimate of ambient flow velocity through the smooth vertical surface; and 6) computing a gas flux estimate from the gas concentration image and the estimate of ambient flow velocity can be performed. The flow velocity estimate can be a single speed and direction estimate, or it can account for variation in speed and/or direction as a function of height above ground. When a height-dependent wind speed is used, the functional form of the wind speed vs. height can be either a fixed functional form, or a form based upon real-time conditions, such as wind speed, solar radiation, terrain, or other atmospheric conditions.

Figure 2:
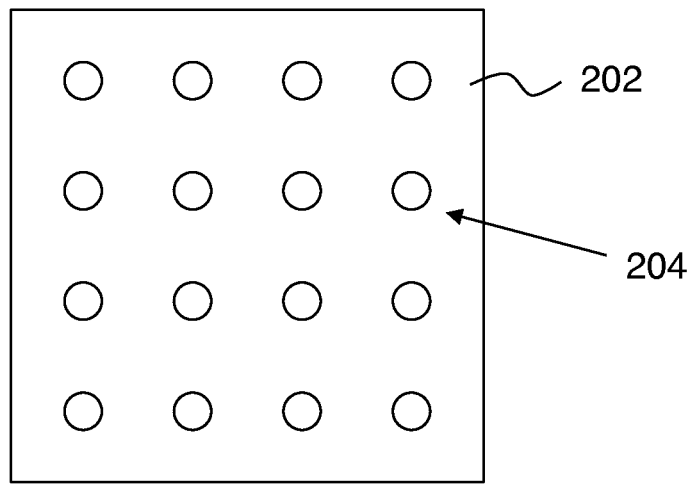
FIG. 2 shows an exemplary 2D array of gas sample inlets.

The measurement locations for gas concentration images can be defined in various ways. One way is to have a 2D array of measurement ports corresponding to the measurement locations. FIG. 2 shows an exemplary 2D array of measurement ports. In this example, an array of measurement ports 204 is provided in member 202 to define the measurement locations. Such an array could be used as a fixed installation, or it could be disposed on a vehicle.

Figure 3:
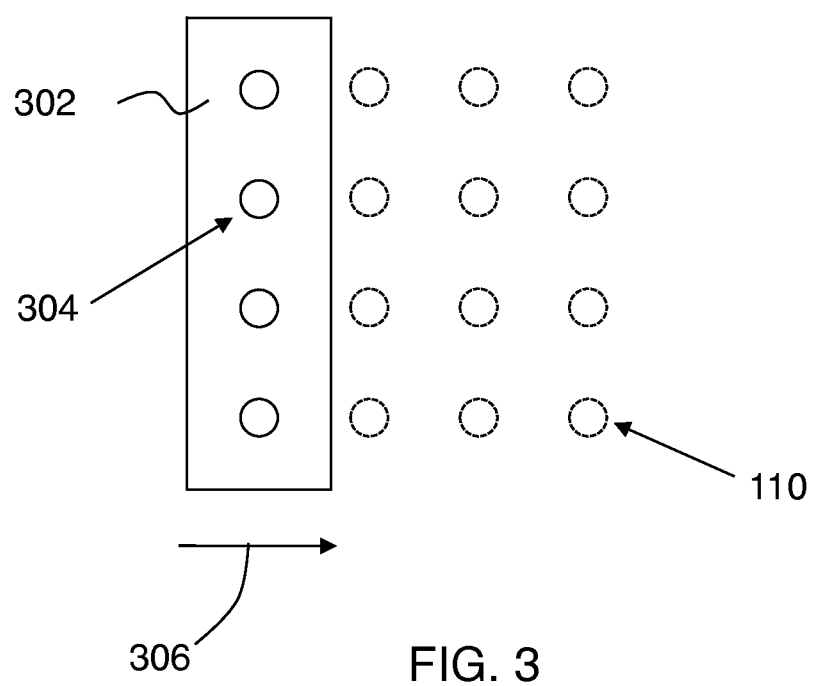
FIG. 3 shows an exemplary 1D array of gas sample inlets configured to be movable through a gas plume.

Another approach for defining the measurement locations is to have a 1D array of measurement ports that can be moved through gas plumes to measure them. FIG. 3 shows an exemplary 1D array of measurement ports configured to be movable through a gas plume. In this example, an array of measurement ports 304 is provided in member 302 to define the measurement locations. As member 302 moves as indicated by arrow 306, a 2D array of measurement locations 110 is defined. For simplicity, FIG. 3 shows a discrete 2D array of measurement locations. It is also possible for the gas samples taken via inlets 304 to be measured continuously, in which case the resulting gas concentration image is still 2-dimensional, but the measurement locations are a set of lines instead of discrete points. This approach is considered in the example of FIGS. 7-9. The resulting gas concentration image is a snapshot in time, to the extent that the transit time of member 302 through the plume is substantially faster than the evolution of the plume in time. Possible evolution of the plume during transit of the vehicle through the plume can lead to over- or under-estimates of the emissions.

In general, the measurement locations can be an array (either Cartesian or non-regular spacing) of ambient air measurement points, distributed on a surface substantially orthogonal to the wind direction. A measurement point can be anything that defines the location of the gas being sampled in a point, line and/or area, such as an inlet of a tube (point), tubes with slots in the side walls (line), and general apertures (area).

When a 1-D array of measurement ports is used to determine a gas concentration image, it is important for the gas concentration measurements to include time information, and to relate the measurement times to measurement positions.

Figure 4A:
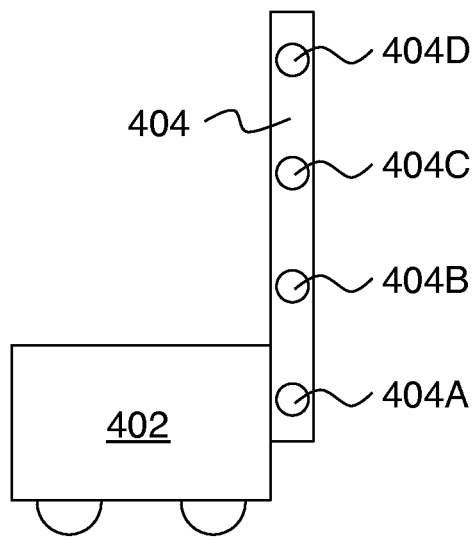
FIGS. 4A-C show examples of 1D arrays of gas sample inlets mounted on a vehicle.

One approach for providing a 1D array of measurement ports that can readily move through a gas plume is to affix a mast to a vehicle. FIG. 4A shows an example, where mast 404 is affixed to vehicle 402. Mast 404 includes measurement ports 404A, 404B, 404C and 404D. This example shows four measurement ports. In general, two or more measurement ports can be employed. The measurement locations are defined by the 1-D array of measurement ports disposed on mast 404 that sweep out a 2-D array of measurement points (discrete points, or a set of continuous lines) as the vehicle moves.

Figure 4B:
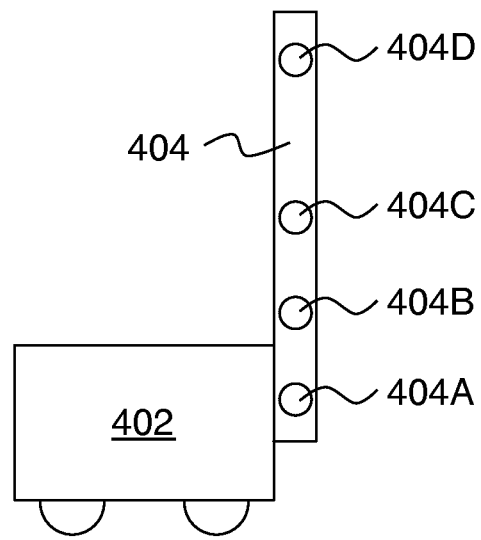

Optionally, the locations of the measurement ports on the mast can be altered during operation and/or adjusted between measurement runs. FIG. 4B shows an example, where the measurement ports on FIG. 4B are in different locations than in the example of FIG. 4A. Optionally, the arrangement of the measurement ports could be changed using a servo system to toggle between two or more predetermined measurement port configurations, or to a configuration where one or more of the measurement ports moves dynamically during the measurement. Optionally, the configuration of measurement ports can include vertically separated measurement ports and one or more additional low-height measurement ports near ground level that can be used specifically to identify on-road below-the-vehicle leaks that are not sufficiently offset from the vehicles axis of motion. It is useful to identify below-the-vehicle leaks, because a leak that is too close to the vehicle's axis of motion will lead to a plume that is not well-formed by the time it is intercepted by the vertical array of measurement points, and the emission rate measurement may be unreliable. The near ground vertical concentration gradient can be used to identify below-vehicle leaks. The near ground horizontal (transverse to the vehicle motion) gradient can also be used to identify below-vehicle leaks.

Figure 4C:
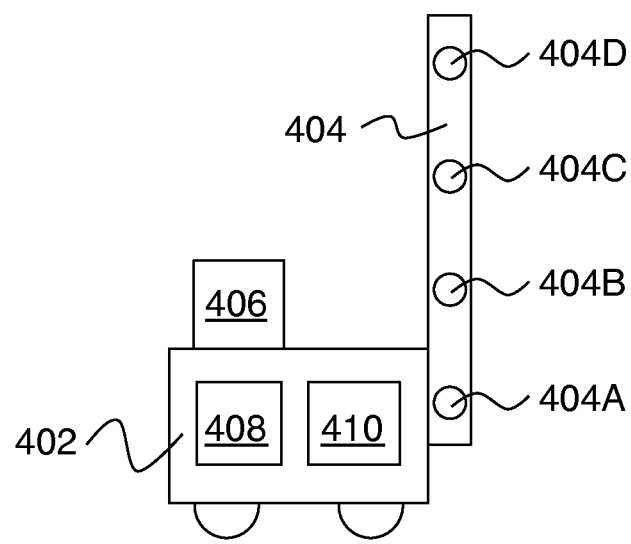

Optionally, further instrumentation can be included on the vehicle 402. FIG. 4C shows an example, where 406 is an instrument for measuring ambient flow velocity, 408 is a global positioning system (GPS) receiver to track horizontal position of the vehicle, and 410 is a vehicle speed sensor and a subsystem for converting time and vehicle speed information to position information. Ambient flow instrument 406 can include a system to relate on-board wind speed and direction measurements to ambient wind speed and direction by accounting for vehicle speed and direction. The on-board wind velocity (i.e., speed and direction) is the vector sum of the ambient wind velocity and the vehicle velocity. It is also possible to include any subset of ambient flow instrument 406, GPS 408 and vehicle speed sensor and subsystem 410. Wind speed and direction can also be obtained from a nearby fixed instrument (e.g., from publicly available weather information). More generally, wind speed, time of day, solar radiation, atmospheric turbulence, or other atmospheric measurements either on the vehicle or nearby can be used to further improve measurement accuracy.

Optionally, two or more masts (each having their own 1D array of measurement ports) can be disposed at the front of the vehicle and separated along the transverse horizontal axis (i.e., along the vehicle width). The recorded gas can be analyzed sequentially using the single analysis instrument, or in parallel with one or more additional analysis instruments. The measurements from each of the masts provide additional measurements of the plume, which can be especially helpful for leaks which are very close to the axis of motion of the vehicle—the plume for the more distant mast may be larger and better formed.

Figure 5:
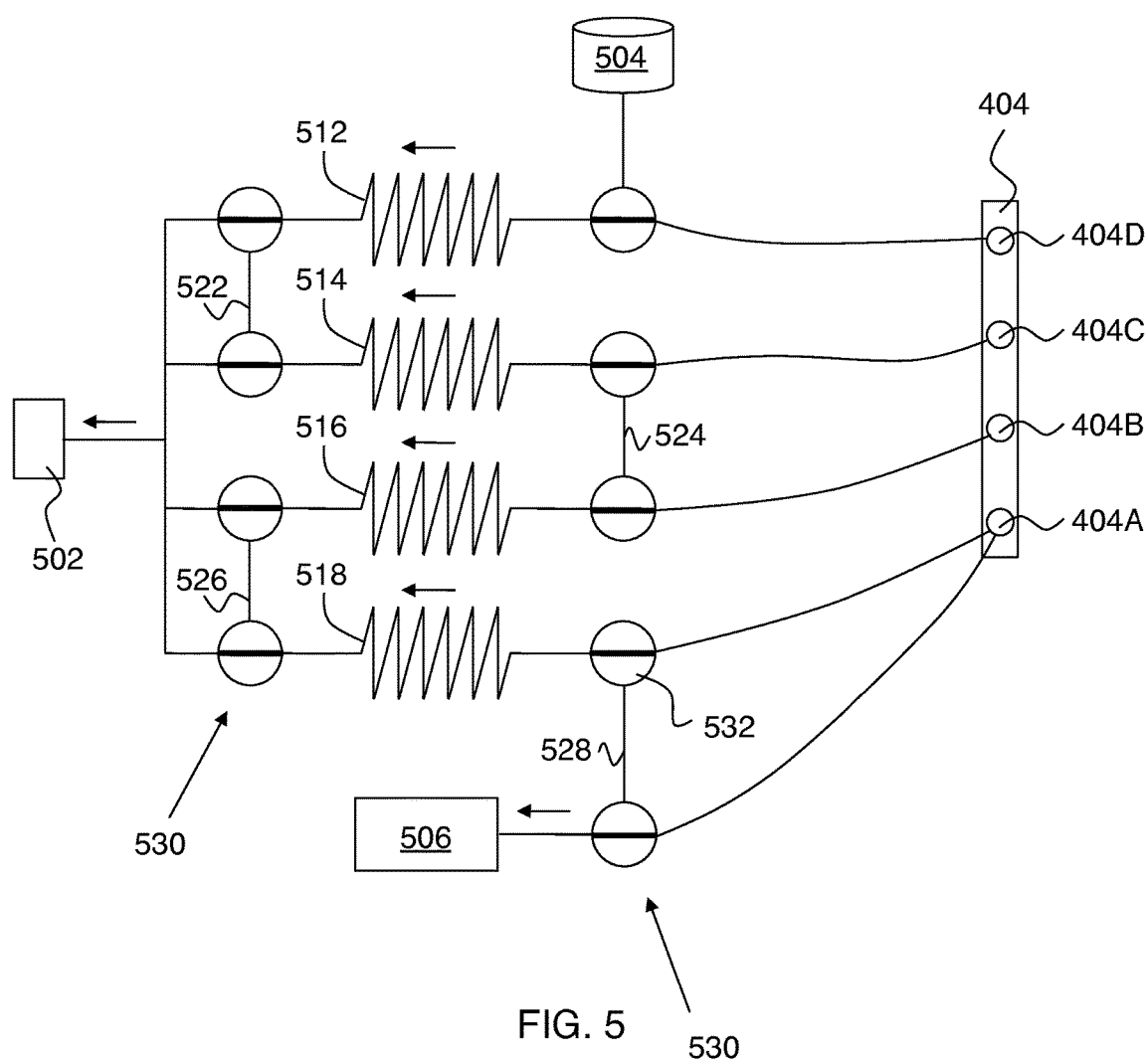
FIG. 5 shows recording mode of an exemplary embodiment of the invention.
Figure 6:
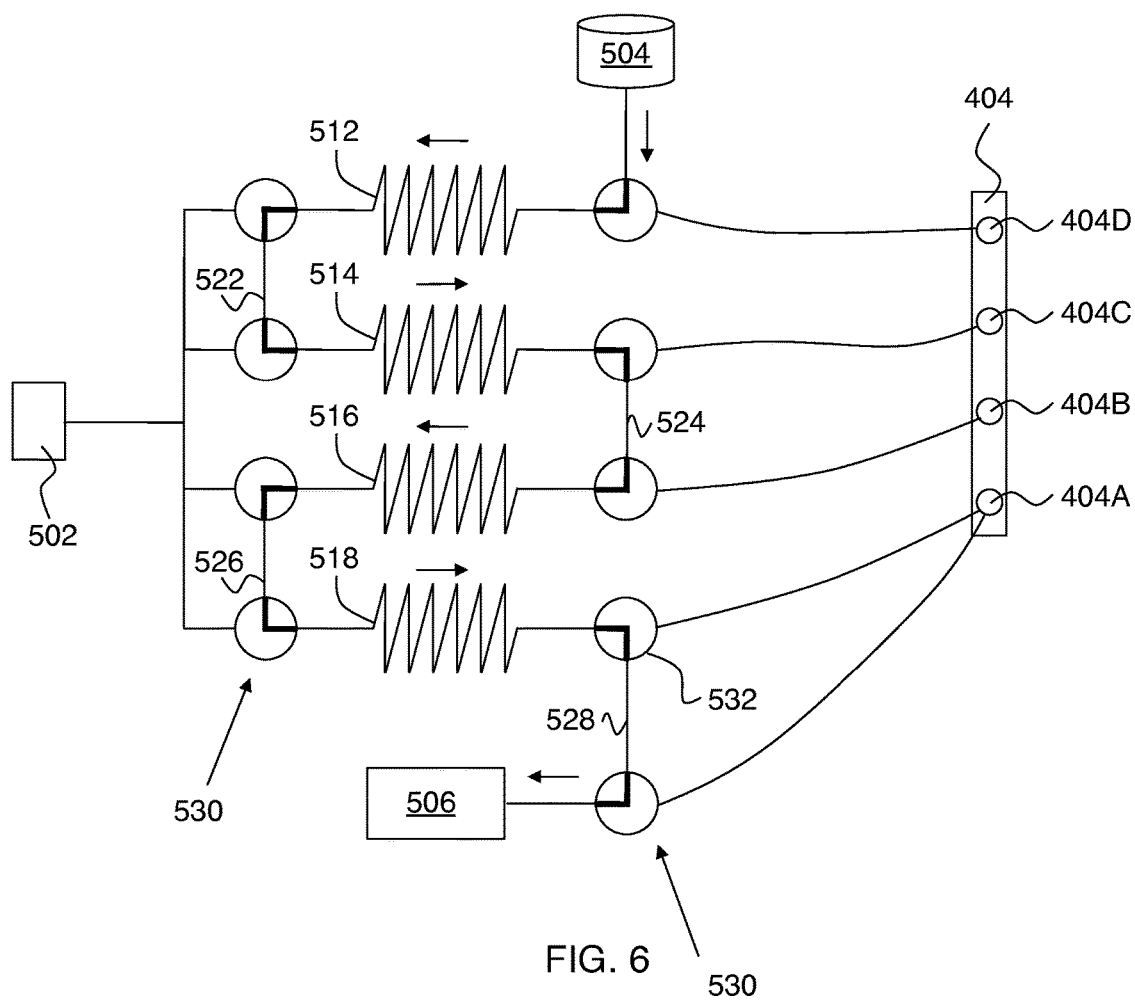
FIG. 6 shows playback mode of an exemplary embodiment of the invention.

FIGS. 5 and 6 show an exemplary embodiment of the invention in recording mode (FIG. 5) and playback mode (FIG. 6). In this example, mast 404 includes measurement ports 404A, 404B, 404C, and 404D. In recording mode (FIG. 5), pump 502 simultaneously draws gas samples from measurement ports 404A, 404B, 404C, and 404D into gas sample storage chambers 518, 516, 514, and 512, respectively. Gas flow control manifold 530 (which includes nine three-way valves, one of which is referenced as 532) is configured to allow this flow, as shown by the heavy lines in the three way valves. Mast 404 is affixed to a vehicle, so the measurement locations defined by the measurement ports are on a smooth vertical surface.

A gas analysis instrument 506 is included, and it receives gas from one of the measurement ports (404A in this example). Any kind of gas analysis instrument can be used. Preferred instruments include cavity enhanced optical spectroscopy instruments, such as cavity ring down spectroscopy (CRDS) instruments and cavity enhanced absorption spectroscopy (CEAS) instruments. In recording mode, gas analysis instrument 506 is mainly used to trigger the switch into playback mode. Any suitable way to trigger playback mode can be used, and practice of the invention does not depend critically on these details (e.g., which of the measurement ports instrument 506 is connected to in recording mode). Optionally, instrument 506 can be used to measure one or more of the measurement ports in real time during the recording phase to ensure that the measurement surface is substantially downwind of the source of emissions.

In playback mode (FIG. 6) the gas flow control manifold 530 is configured to provide the two or more gas samples sequentially to the gas analysis instrument to provide gas concentration data points. This is shown by the heavy lines in the three way valves on FIG. 6.

The system is configured to relate the gas concentration data points to the two or more measurement locations to provide a gas concentration image of the smooth vertical surface, as described above.

More generally, outputs from this measurement can include one or more of the following: 1) An estimate of the emissions transported by the wind through the surface defined by the measurement points, either averaged over the time period of the measurement, or reported with the time resolution of the device, determined by a) the response time of the instrument, b) the ratio of flows between recording and playback, and c) time dispersion of gas in the tubes during recording and playback; 2) An image of the concentration measured on the surface, averaged over the time period of the measurement; or 3) A video of the concentration measured on the surface, as it evolved during the time period of the measurement.

The number of gas sample storage chambers is limited only by the number of 3-way valves (two are needed per gas sample storage chamber), the speed of the analysis instrument, the desired duty factor of the measurement, and the potential for pulse spreading within the tubing (which is negligible for most practical situations). Pulse spreading is likely to be most serious during high flow rate playback.

Preferably, the gas sample storage chambers are configured as tubes having a length to diameter ratio of 20:1 or more (more preferably 100:1 or more). This high aspect ratio usefully provides a time axis for gas samples in the gas sample storage chambers. Further details on this concept of preserving a time axis in gas samples in narrow tubes are given in U.S. Pat. No. 7,597,014, filed Aug. 15, 2006, and hereby incorporated by reference in its entirety.

Optionally, plumbing manifold 530 can include volumetric or mass flow sensors located on each of the recording lines and/or the analysis line, so that accurate time reconstruction is possible given the valve switching times and the molar volumes contained in the gas manifold and connection tubing. This can make the system more robust to unexpected conditions (pressures, flow conductivity, etc.) in the plumbing system.

For time efficiency, the flow rate through the gas analysis instrument during playback mode is preferably larger than the flow rate through the gas sample storage chambers during recording mode. Precise flow sensing or control can be used to maintain the integrity of the time axis for the several gas samples, and to make sure that all of the gas sample storage chambers are filled with gas that corresponds to the same period of time.

It is preferred for the system to include a push gas source 504, as shown on FIGS. 5 and 6. Provision of a predetermined push gas during playback, as opposed to just allowing ambient in during playback can provide significant advantages. The most important advantage is the ability to use the push gas to identify the transitions between the various gas samples being analyzed in playback mode. This can be accomplished by having the push gas separate the gas samples when they are provided to the gas analysis instrument 506. For example, trapped push gas in tubing 522, 524, 526 and 528 can provide such separation. Push gas can be trapped in these sections of tubing by performing a complete playback of all gas samples until push gas is the only gas present in the system. After that, switching to recording mode (FIG. 5) will trap push gas in tubing 522, 524, 526 and 528. The push gas is preferably distinguishable from the gas samples using results from the gas analysis instrument.

The push gas can be distinguished from the gas samples by having a different concentration of the primary gas (i.e., the gas which is being measured in ambient) than is possible in the gas samples and/or by including a secondary gas species which the gas analysis instrument is responsive to and which is not expected to occur in the gas samples. The optional use of a secondary gas species in the push gas can avoid disrupting the primary measurement by changing concentration of the primary species in the push gas.

Optionally, the push gas concentration can be below ambient concentration levels, so that this low signal is unique to the push gas and will not exist under reasonable conditions in the recorded ambient gas, thus giving a clear signature for identification of the timing pulses provided by the push gas. Optionally, zero air (i.e., ambient air filtered to contain less than 0.1 ppm total hydrocarbons) can be the push gas, or zero air can be used to dilute ambient air to provide the push gas. Optionally, the component of the push gas used to provide the timing information can be $CO_2$.

Optionally, the push gas can be ambient air that is subsequently treated by a sodalime, ascarite, or other $CO_2$ trap to reduce the $CO_2$ concentration below ambient levels.

Optionally, the push gas concentration can be above ambient concentration levels. Optionally, a high concentration of the push gas species can be contained in a semipermeable container, such as a section of PTFE (polytetrafluoroethylene) tubing, such that slow diffusion of the gas from the container into a sample of ambient air provides the push gas for timing measurement.

The example of FIGS. 5 and 6 shows providing the two or more gas samples sequentially to the gas analysis instrument by connecting the gas sample storage chambers to each other in series and flowing the gas samples to the gas analysis instrument. Alternatively, the two or more gas samples can be provided sequentially to the gas analysis instrument by sequentially switching the gas sample storage chambers to flow to the gas analysis instrument (e.g., with an N-way valve for N gas sample storage chambers). As another alternative, banks of measurement ports can be measured serially, with different banks being selected by a multi-position valve at the inlet of instrument 506. Such use of banks of measurement ports can mitigate the gas dispersion in the gas sample storage chambers, because the sample in the last gas sample storage chamber (e.g., 512 on FIG. 6) does not need to be transported through all the other gas sample storage chambers before it reaches the measurement instrument.

Figure 7:
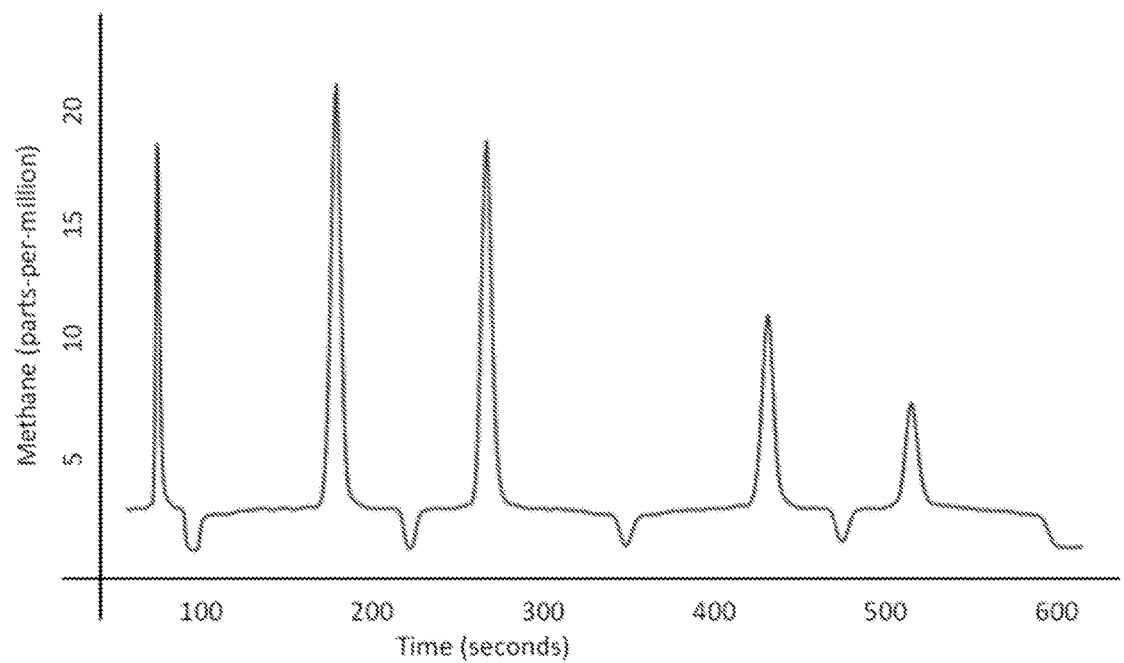
FIG. 7 shows an exemplary playback signal.
Figure 8:
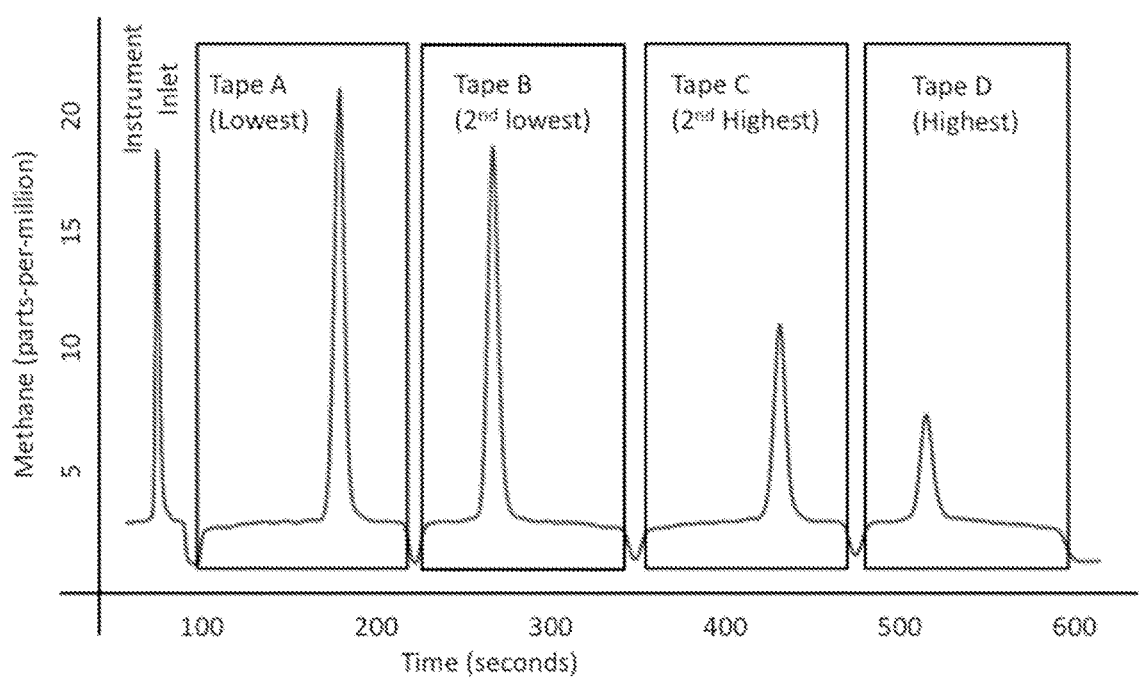
FIG. 8 shows how the various parts of the signal of FIG. 7 are related to the gas sample inlet ports.
Figure 9:
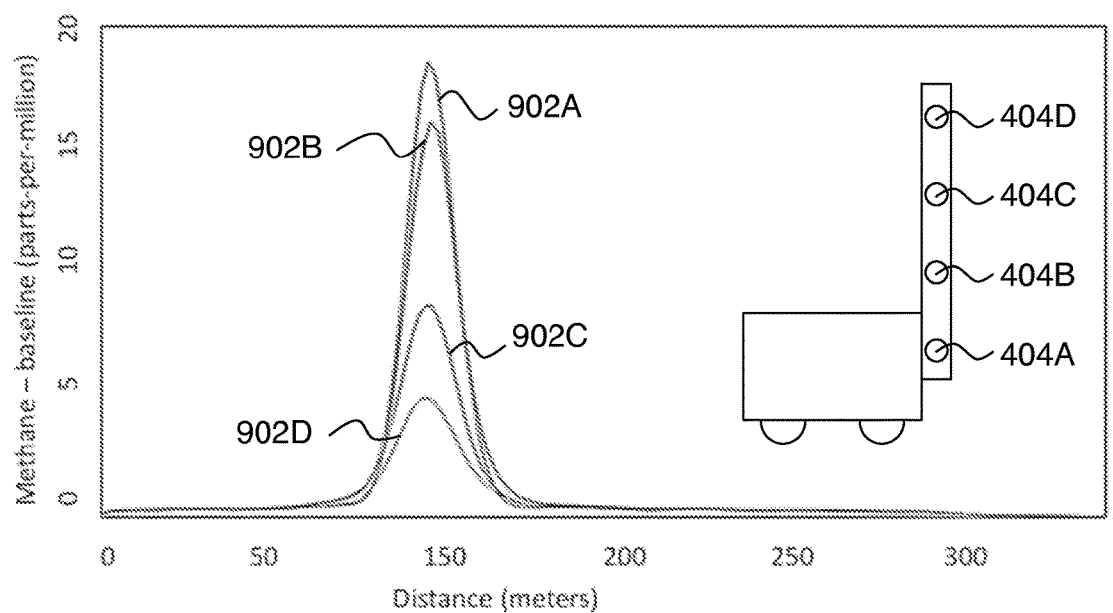
FIG. 9 shows the results of FIGS. 7 and 8 related to a common horizontal position axis.

Important features of the present approach can be better appreciated by considering the data of FIGS. 7-9. FIG. 7 shows a playback signal from a 4-channel system as in FIGS. 5 and 6. In this exemplary system, gas sample storage chambers 512, 514, 516, and 518 have capacity 500 scc (standard cubic centimeter), and the recording flow rate is 1000 sccm (standard cubic centimeters per minute). Thus, the gas sample storage chambers each provide 30 seconds of stored gas sample. FIG. 8 shows how the various parts of the signal of FIG. 7 are related to the gas sample inlet ports. Here Tape A relates to measurement port 404A, Tape B relates to 404B, etc. The dips in the measured concentration are from trapped push gas that separates the samples. Here it is clear that the time axis for Tape B is reversed relative to the time axis for Tape A, which is consistent with the opposite flow directions through gas sample storage chambers 516 and 518 shown on FIG. 6. Similarly, the time axis of Tape D is reversed with respect to Tape C, while Tape A and Tape C have consistent time axes. All of this is consistent with the flow directions through gas sample storage chambers 512, 514, 516, and 518 on FIG. 6.

FIG. 9 shows the results of FIGS. 7 and 8 where time has been converted to position, thereby relating the four gas samples to a common horizontal position axis. This information can be used to provide a 2D gas concentration image for the plume, which in this example gave a source flux estimate of 1.5±0.3 L/s based on a wind speed estimate of 2.5 m/s (normal to the measurement surface) and a vehicle speed of 10.8 m/s.

In some cases, it is preferred to account for wind speed, especially the variation of wind speed with height. If the wind speed does not vary with vertical position, the following simplification can be made to Equation 1:

$$Q(t) = \int_A k(C(x, y, t) - C_0)\overrightarrow{u(x, y, t)} \cdot \hat{n} \, dA \quad (2)$$
$$= \int_D kH(\Gamma(x, t) - C_0)\overrightarrow{u(x, t)} \cdot \hat{n} \, dx$$

where $\Gamma(x, t) = \frac{1}{H}\int_0^H C(y)\,dy$.

Figure 10A:
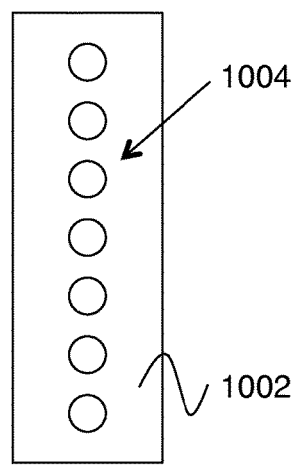
FIGS. 10A-C show exemplary line pixel configurations.

In other words, $\Gamma$ is the average concentration vertically. Measurement of the average vertical concentration could be accomplished with a 'line pixel' which responds by drawing a constant amount of gas per unit distance vertically that is analyzed with a single gas analyzer. One example of a line pixel is shown on FIG. 10A, where a section of tubing 1002 has identical holes 1004 drilled in the wall that are distributed evenly vertically. The flow through each hole is the same, thus leading to an even weighting of the concentration reported by an analyzer measuring the combined flow from all the individual holes.

However, under typical conditions, the wind field is not constant vertically. Various models have been used for wind speed vs. height. For example, one model is a power law with height of the following form:

$$u(y) = u_0 \left(\frac{y}{y_0}\right)^\alpha \quad (3)$$

where $\alpha$ is typically 0.1 to 0.2. As can be seen, this is a fairly weak dependence on height, except very close to the ground, where the wind drops to zero as expected.

Another model for the wind profile is logarithmic:

$$\frac{u(y)}{u(y = y_0)} = \ln\left(\frac{y}{y_{surface}}\right) \Big/ \ln\left(\frac{y_0}{y_{surface}}\right) \quad (4)$$

Here, $y_{surface}$ is a scaling parameter related to the roughness of the ground surface. For typical values of $y_{surface}$ of at most a few centimeters, this profile also has a weak dependence on height except near the ground, as with the power law form.

A line pixel with evenly spaced inlet points of equal flow (i.e., a 'balanced' line pixel as shown on FIG. 10A) can lead to biased results, depending upon where the centroid and extent of the plume intersects the balanced line pixel. For example, the flux of a plume that strikes the pixel close to the ground would be overestimated. Conversely, a plume that strikes the balanced line pixel high would be underestimated.

However, it is possible to create a line pixel where the vertical responsivity of the pixel is tailored to compensate for the vertical wind gradient. In other words, if a line pixel is constructed such that it responds with a weighted average concentration $$\Gamma_{weighted}(x, t) = \frac{1}{H}\int_0^H C(y)\left(\frac{y}{y_0}\right)^\alpha dy,$$

then the emissions integral simplifies to $$Q(t) = \int_D kH(\Gamma_{weighted}(x,t) - C_0)\overrightarrow{u_0(x,t)} \cdot \hat{n}\,dx \quad (5)$$

Figure 10B:
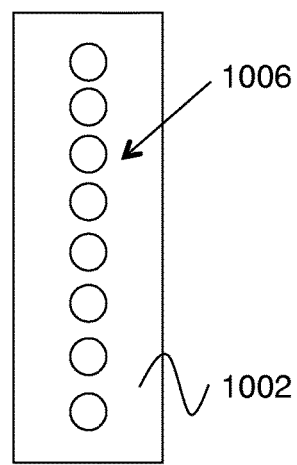
Figure 10C:
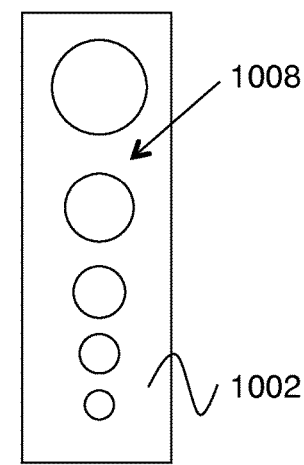

The weighting function is the same power law that determines the vertical wind speed gradient, and can be accomplished practically, for example, by drilling holes with the same diameter but with a higher density at higher elevations (e.g., holes 1006 on FIG. 10B), or with larger diameters at higher elevations (e.g., holes 1008 on FIG. 10C), such that the flow into the line pixel/unit height follows the same power law. Similar compensation can be done for the logarithmic model of Equation 4, or for any other wind speed model. Other means of achieving a tailored profile of flow/unit height are also possible, such as active flow control devices (e.g., proportional flow valves, pulse width modulated valves, or a spatially selective activation of vertically disposed on-off valves to achieve an effective flow/unit height); in addition, passive flow control devices downstream of the physical inlet (e.g., orifices, critical flow orifices, or long tubing lengths), alone or in combination, can be used with a wide range of inlet sizes to achieve the specified flow condition. The inlet flow rates of the various contributions to a line pixel can be altered in operation using active flow control devices.

The spatial density scale for which inlets can be effectively grouped for the purposes of determining flow/unit height is the typical size of a plume, which is 0.1-10 m under most practical conditions.

It is also a significant advantage if a plume presented simultaneously to all the inlet ports be delivered simultaneously when the flows are combined and the gas is brought to the analyzer. This allows the system to quantify the flux with high spatial resolution, which is a significant advantage when emissions sources are close together. The simplest form of array inlets, i.e., a tube perforated periodically or aperiodically by small holes, does not achieve this goal, since gas which enters at the far end of the perforated tube has a significantly longer transit time to the instrument than gas which enters at the near end of the tube. One way to accomplish this goal is to equalize the transit time of the tubing from each of the inlets to the instrument, where the transit time is given by the volume per unit length of the tubing divided by the volumetric flow of that inlet. The transit time is proportional to the tubing length for equal flow systems, but is inversely proportional to the flow of each inlet.

Figure 11:
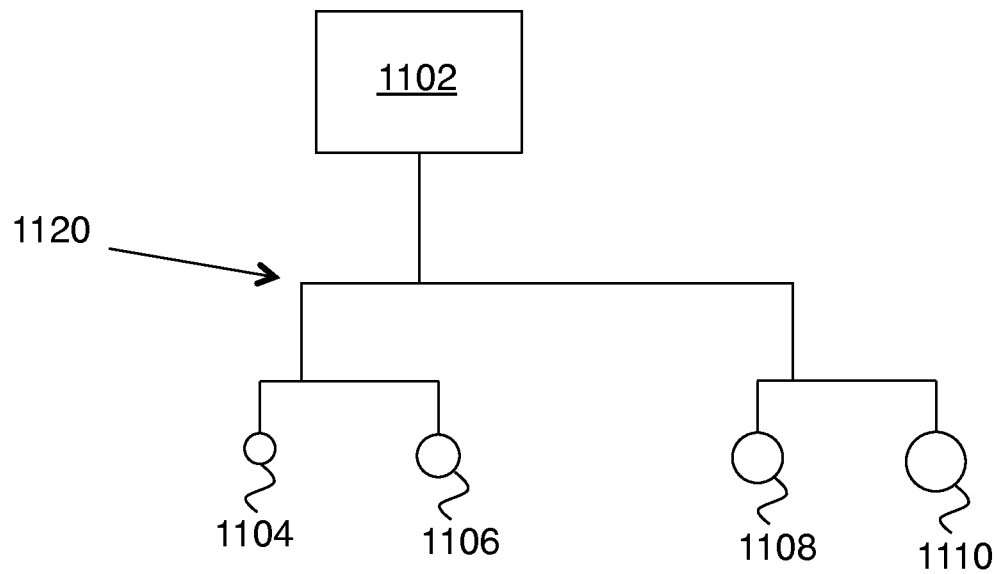
FIG. 11 shows an example of transit time equalization within a line pixel.

There are other, more efficient and practical configurations. In FIG. 11, the lengths of tubing 1120 are arranged such that the higher flow inlets have longer transit paths before they are combined into instrument 1102. For example, high-flow inlet 1110 has the longest transit path, low-flow inlet 1104 has the shortest transit path, and inlets 1106 and 1108 have intermediate length transit paths according to their respective flow rates. The tree-like arrangement of the branching makes for an efficient use of tubing. The example of FIG. 11 is a binary tree, but $3^{rd}$ and higher order trees are also possible.

Figure 12:
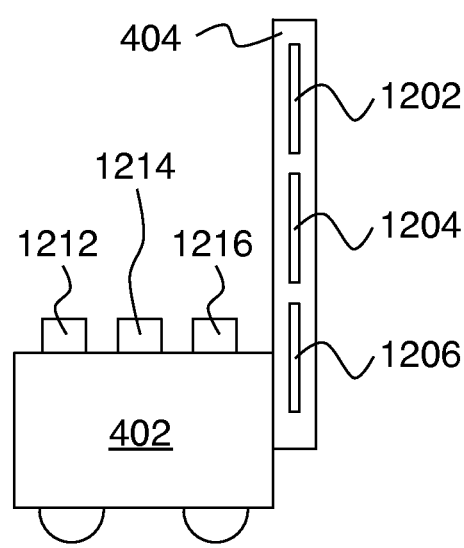
FIG. 12 shows an example of gas collection via multiple line pixels.

In some cases, where the plume flux is spread over a large range of vertical positions, it is advantageous to have two or more flow-weighted line pixels, situated each above the next, with separate analyzers measuring each. The flow into the inlets of each line pixel is arranged such that the vertical dependence of the integrand is removed for that line pixel, and the flux from each plane swept out by a line pixel is computed separately and summed. This has two advantages: first, it avoids the problem of encompassing a wide dynamic range of wind speeds with the same wide dynamic range of flows, and second, it increases the sensitivity of the system to plume structures close to the ground, where the advective wind flow is low but the concentration can be high. FIG. 12 schematically shows such a configuration, where mast 404 includes line pixels 1202, 1204 and 1206, each connected to a separate gas analysis instrument (1212, 1214, and 1216 respectively).

Line pixels as described here can be used as the measurement ports of any previously described embodiment. The resulting output need not be a gas concentration image. Instead, gas measurement results from line pixels can be useful for obtaining gas flux results from the measured data with reduced post-processing and/or fewer independent gas analysis instruments, which can expedite gas leak identification. In particular, such line pixels can aggregate nearby inlet locations to perform analog averaging of the concentration signals without the need to independently measure each location individually.

The invention claimed is:

1. A method for performing gas concentration measurements in an ambient, the method comprising:
    simultaneously collecting two or more gas samples from two or more measurement locations,
    wherein the measurement locations are configured to be on a smooth vertical surface,
    wherein the measurement locations are defined by two or more measurement ports that are moved along the smooth vertical surface,
    providing the two or more gas samples to a gas analysis instrument to provide gas measurement results; and
    providing the gas measurement results as an output;
    wherein gas contributions from all of the two or more measurement ports are combined to provide a single input to the gas analysis instrument via a gas flow control manifold;
    wherein the measurement ports and the gas flow control manifold are configured to provide equal transit time for all of the gas contributions from their corresponding measurement port to the input to the gas analysis instrument;
    wherein the measurement ports are configured to have inlet flow and/or inlet spacing that provide a weighting of contributions according to vertical height.

2. The method of claim 1, wherein the measurement ports are configured to have equally spaced apertures having equal flow.

3. The method of claim 1, wherein the weighting increases with vertical height.

4. The method of claim 1, wherein the weighting is in accordance with a wind speed model.

5. The method of claim 1, wherein the equal transit time is provided by a tree-like arrangement of gas tubing.

6. The method of claim 1, further comprising providing a gas flux estimate from the gas measurement results.

7. The method of claim 1, wherein the measurement ports are configured to have flow rates for the measurement ports that provide an accurate average for estimating gas flux.

8. A system for performing gas concentration measurements in an ambient, the system comprising:
    a gas flow control manifold configured to collect two or more gas samples from two or more measurement locations;
    wherein the measurement locations are configured to be on a smooth vertical surface,
    wherein the measurement locations are defined by two or more measurement ports that are moved along the smooth vertical surface, and
    a gas analysis instrument;
    wherein gas contributions from all of the two or more measurement ports are combined to provide a single input to the gas analysis instrument via the gas flow control manifold;
    wherein the measurement ports and the gas flow control manifold are configured to provide equal transit time for all of the gas contributions from their corresponding measurement port to the input to the gas analysis instrument;

wherein the measurement ports are configured to have inlet flow and/or inlet spacing that provide a weighting of contributions according to vertical height.

9. The system of claim 8, further comprising a mast configured to be affixed to a vehicle, wherein the measurement ports are disposed on the mast.

10. The system of claim 9, further comprising a global positioning system (GPS) receiver to track horizontal position of the vehicle.

11. The system of claim 9, further comprising a vehicle speed sensor and a subsystem for converting time and vehicle speed information to position information.

12. The system of claim 8, wherein the measurement ports are configured to have equally spaced apertures having equal flow.

13. The system of claim 8, wherein the weighting increases with vertical height.

14. The system of claim 8, wherein the weighting is in accordance with a wind speed model.

15. The system of claim 8, wherein the inlet flow of the contributions can be altered in operation.

16. The system of claim 8, wherein the equal transit time is provided by a tree-like arrangement of gas tubing.

* * * * *